United States Patent [19]

Janda et al.

[11] Patent Number: 5,444,155
[45] Date of Patent: Aug. 22, 1995

[54] MOLECULES WITH ANTIBODY COMBINING SITES THAT INDUCE ASYMMETRY

[75] Inventors: Kim Janda, San Diego; Richard A. Lerner, La Jolla, both of Calif.; Samuel J. Danishefsky, New Haven, Conn.

[73] Assignee: The Scripps Research Institute, La Jolla, Calif.

[21] Appl. No.: 757,442

[22] Filed: Sep. 10, 1991

[51] Int. Cl.6 .................. A61K 35/14; C02K 3/00; C12N 5/00
[52] U.S. Cl. .................. 530/388.1; 530/387.1; 435/240.26; 435/240.27; 435/135; 435/146; 435/188.5; 435/196
[58] Field of Search .................. 435/240.26, 240.27, 435/174, 197, 212, 68, 172.2, 69.1, 70.21, 240.2; 530/188.5, 387.1, 388.1, 391, 806, 808; 424/85.8

[56] References Cited

U.S. PATENT DOCUMENTS

| | | | |
|---|---|---|---|
| 4,342,566 | 2/1980 | Theofilopoulos et al. | 422/57 |
| 4,361,549 | 11/1982 | Kung et al. | 424/85 |
| 4,659,567 | 4/1987 | Tramontano et al. | 424/85 |
| 4,792,446 | 12/1988 | Kim et al. | 424/85 |
| 4,888,281 | 12/1989 | Schochetmann et al. | 435/72 |
| 5,030,717 | 7/1991 | Tramontano et al. | 530/387 |

OTHER PUBLICATIONS

Vladyko et al. (1990) Vopr. Verusol. vol. 35, 6. pp. 448–492.
Slobin, *Biochemistry*, 5:2836–2844 (1966).
Kohnen et al., *Febs Letters*, 100:137–140 (1979).
Kohnen et al., *Biochim. Biophys. Acta*, 629:328–337 (1980).
Kohnen et al., *Febs Letters*, 111:427–431 (1980).
Jencks, W. P., *Catalysis in Chemistry and Enzymology*, p. 288 (McGraw-Hill, New York 1969).
Lerner, Tramontano and Janda *Science*, 234, 1566 (1986).
Pollack, Jacobs and Schultz, *Science*, 234, 1570 (1986).
Leon et al., *Biochem.*, 10, 1424 (1971).
Jacobs et al., *J. Am. Chem Soc.*, 109, 2174 (1987).
Benkovic et al., *Proc. Natl. Acad. Sci. USA*, 85:5355 (1988).
Jackson et al., *J. Am. Chem. Soc.*, 110:4841 (1988).
Napper et al., *Science*, 237:1041 (1987).
Hilvert et al., *Proc. Natl. Acad. Sci. USA*, 85:4955 (1988).
Jencks, W. P., *Adv. Enzymology*, 43, 219 (1975).
Pauling, L., *Amer. Scientist*, 36, 58 (1948).
Leinhard, G., *Science*, 180, 149 (1973).
Wolfenden, R., *Acc. Chem. Res.*, 5, 10 (1972).
Jencks, W. P., *XVII International Solvay Conference (Nov. 1983)*.
Kohler and Milstein, *Nature*, 256, 495 (1975).
Bartlett, et al., *Biochemistry*, 22, 4618 (1983).
W. P. Jencks, *Catalysis in Chemistry and Enzymology*, ch. 10, (McGraw-Hill, New York, 1969).
Westerik et al., *J. Biol. Chem.*, 247, 8195 (1972).
R. C. Thompson, *Biochemistry*, 12, 47 (1973).
Imperali et al., *Biochemistry*, 25, 3760 (1986).
Weaver et al., *J. Mol. Biol.*, 114, 119 (1977).
Jacobsen et al., *J. Am. Chem. Soc.*, 103, 654 (1981).
W. N. Lipscomb, *Acc. Chem. Res.*, 15, 232 (1982).
Christianson et al., *J. Am. Chem. Soc.*, 108, 545 (1986).
L. M. Sayre, *J. Am. Chem. Soc.*, 108, 1632 (1986).
Liu et al., *Biochem.*, 80, 690 (1979).
Niman et al., *Proc. Natl. Acad. Sci. USA*, 77, 4524 (1980).
Niman et al., in *Monoclonal Antibodies and T-Cell Products*, Katz, D. H. Ed., 23–51, CRC Press, Boca Raton, Fl (1982).
Shulman et al., *Nature*, 276, 269 (1978).
Galfre et al., *Nature*, 277, 131 (1979).

(List continued on next page.)

*Primary Examiner*—Garnette D. Draper
*Assistant Examiner*—Gian P. Wang
*Attorney, Agent, or Firm*—Welsh & Katz, Ltd.

[57] ABSTRACT

Monoclonal antibodies or paratope-containing portions thereof are disclosed that immunoreact with a meso diester substrate ligand and catalytically hydrolyze a single predetermined ester bond to form one of a pair of enantiomers. Methods of making and using the same are also disclosed.

2 Claims, No Drawings

OTHER PUBLICATIONS

Goding, "Production of Monoclonal Antibodies by Cell Fusion," in *Antibody as a Tool*, Marchanlonis et al., eds. John Wiley & Sons Ltd., p. 273 (1982).
Engvall, E., *Methods Enzymol.*, 70, 419 (1980).
Stedman et al., *Biochem. J.* 26:2056 (1932).
Alles et al., *Biol. Chem.*, 133: 375 (1940).
Laemmli, V. *Nature*, 227: 680 (1970).
Neuberger et al., *Nature*, 312:604–8 (1984).
Ochi et al., *Proc. Natl. Acad. Sci, USA*, 80:6351–55 (1987).
Oi et al., *Proc. Natl. Acad. Sci. USA*, 80:825–29 (1983).
Roberts et al., *Protein Engineering*, 1:59–65 (1986).
Wood et al., *Nature*, 314:446–9 (1985).
Deardoff et al., *Tetrahedron Letter.*, 27, 1255 (1986).
Johnson et al., *J. Am. Chem. Soc.*, 111, 3456 (1989).
Chow et al., *J. Org. Chem* 54, 6016 (1989).
Wilson et al., *Proc. Natl. Acad. Sci. USA*, 71, 3194 (1974).
Tijssen, P. in *Practice and theory of Enzyme Immunology* (Burden et al., eds), Elsevier Press: New York, p. 3941, (1987).
Fujii et al., *J. Am. Chem. Soc.*, 113:8528–8529 (1991).
Janda et al., *Science*, 244:437–440 (1989).
Ikeda et al., *J. Am. Chem. Soc.*, 113:7763–7764 (1991).
J. Hine, *Physical Organic Chemistry*, McGraw-Hill Book Co., Inc., New York (1962) pp. 275–279.
*Grant & Hackh's Chemical Dictionary*, 5th ed., McGraw-Hill Book Co., Inc. New York (1987) p. 363.

MOLECULES WITH ANTIBODY COMBINING SITES THAT INDUCE ASYMMETRY

This invention was made with government support under Contract Nos. GM 43858 and HL 25848 awarded by the National Institutes of Health. The government has certain rights in the invention.

DESCRIPTION

1. Technical Field

The present invention relates to antibodies, antigens and immunogens, and more particularly to paratope-containing molecules that catalyze the hydrolysis of a preselected prochiral ester bond and induce asymmetry by that hydrolysis.

2. Background of the Invention

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trypsin. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding can lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively.

Slobin, *Biochemistry*, 5:2836–2844 (1966) reported preparing antibodies to a p-nitrocarbobenzoxy conjugate of bovine serum albumin. Those antibodies were thereafter used to hydrolyze p-nitrophenyl acetate and epsilon-aminocaproate esters. The reaction of the acetate ester was described by a second-order rate constant and was said to appear to be nonspecific. The second-order rate constant obtained using normal gamma globulin was said to be about equal to that of the specially prepared antibodies. The presence of the specially prepared antibodies was said to inhibit the hydrolysis of the aminocaproate ester.

Kohnen and coworkers also reported attempts using antibodies to catalyze esterolysis. The antibodies utilized by this group were, in each instance, raised to a portion of the ultimately utilized substrate molecule that did not contain the bond to be hydrolyzed.

In their initial work [*FEBS Letters*, 100:137–140 (1979) and *Biochim. Biophys. Acta*, 629:328–337 (1980)] anti-steroid antibodies were used to hydrolyze 7-umbelliferone (7-hydroxycoumerin) esters of a carboxyethyl thioether of asteroid. In each instance, an increase in hydrolytic rate was observed as compared to background or to a rate obtained with normal IgG. In both instances, turn over numbers were low (about one mole of substrates per mole of antibody per minute, or less), and the reaction rates declined with time, reaching a plateau with saturation of the antibody. That slow down in rate was attributed to an irreversible binding of the steroidal acid product to the antibody.

Kohen et al. also reported hydrolysis of 7-[-N-(2,4-dinitrophenyl)-6-aminohexanoyl]-coumerin using monoclonal antibodies raised to the dinitrophenyl portions of that substrate molecule [*FEBS Letters*, 111:427–431 (1980)]. Here, a rate increase over background was also reported, but the reaction was said to be stoichiometric rather than catalytic. A decrease in rate that approached zero was reported as saturation of the antibody was reached. Again, the decrease was attributed to product inhibition caused by binding of the product acid to the antibody since some of the initial hydrolysis activity could be regenerated by chromatography of an antibody-substrate-product mixture.

When strong antibody binding is directed to stable states of substrate molecules, the slow rate of dissociation of the complex will impede catalysis. Such is thought to be the situation for the results reported by Kohnen and coworkers.

The above constructs, though interesting, are severely limited by the failure to address the mechanism of binding energy utilization which is essential to enzymes [W. P. Jencks, *Adv. Enzymol.*, 43, 219 (1975)].

Those deficiencies can be redressed by using a transition state analog as the hapten to elicit the desired antibodies. This hapten (also referred to herein as an "analog-ligand") can assume the role of an inhibitor in the catalytic system.

Thus, immunological binding can be used to experimentally divert binding interactions to catalytic processes. For example, it was suggested that use of an antibody to a haptenic group that resembles the transition state of a given reaction should cause an acceleration in substrate reaction by forcing substrates to resemble the transition state. Jencks, W. P., *Catalysis in Chemistry and Enzymology*, page 288 (McGraw-Hill, New York 1969). Notwithstanding that broad suggestion, specific transition state haptens were not suggested, nor were specific reactions suggested in which the concept might be tested.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful mental constructs that by definition, cannot be isolated, as compared to intermediates, which are isolatable.

Although the above hydrolytic transition states cannot be isolated, a large amount of scientific literature has been devoted to the subject. Some of that literature is discussed hereinafter.

Whereas the before-described transition state for amide and ester hydrolyses is believed to be well understood, the parameters of the topology, e.g., size, shape and charge, of receptor binding sites in which particular amides, such as proteins, or esters, such as fats, react through those transition states is not as well understood.

It would therefore be beneficial if the topology of a plurality of binding sites were known so that the interactions of the ligands that bind in those sites could be studied. Unfortunately, the topology of receptor binding sites in biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose location is known, the chemical identity, i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolytic proteases typically cleave their substrates, polypeptide chains, adjacent to a particular amino acid residue that may occur several times in the polypeptide chain of the protein. While such relatively random cleavage can be useful in obtaining a polypeptide map of the protein, that relatively random cleavage is not as useful where particular amino acid residue sequences are desired to be produced.

For example, modern genetic engineering techniques have been useful in preparing fusion proteins that contain a desired protein or polypeptide fused to the translation product of a vector gene such as the lac z gene. The use of such fusion proteins is, however, hindered by the presence of fragments of the vector gene product. It would also therefore be beneficial if proteolytic enzyme-like molecules could be developed that would cleave such fusion products between the wanted and unwanted fusion polypeptide or protein portions.

Recently, Lerner, Tramontano and Janda [*Science*, 234, 1566 (1986)] reported monoclonal antibodies to hydrolyze esters in U.S. Pat. No. 4,656,567. Pollack, Jacobs and Schultz [*Science*, 234, 1570 (1986)] reported a myeloma protein denominated MOPC167 [Leon et al., *Biochem.*, 10, 1424 (1971)] that catalyzes the hydrolysis of a carbonate.

In the two Lerner and Tramontano disclosures, the antibodies were raised to a phosphonate that was synthesized to represent a stable analog of the tetrahedral hydrolytic transition state of the carboxylic acid ester or carbonate ester. The Pollack et al. antibody principally discussed was a myeloma protein that happened to bind to a phosphonate that was structurally analogous to the carbonate analog hydrolyzed. Thus, in the Lerner and Tramontano et al. work, the substrate to be hydrolyzed was preselected, with the immunizing analog and hydrolytic antibodies being synthesized in accordance with the desired product. Pollack et al. designed the substrate to be hydrolyzed once they knew the specificity of the myeloma protein. Pollack et al. also reported (above) the existence of a catalytic antibody, substrated and analog substrate system for carbonate hydrolysis similar in concept to that of Lerner et al. Work relating to that system is reported in Jacobs et al., *J. Am. Chem Soc.*, 109, 2174 (1987).

U.S. Pat. No. 4,888,281 (Schochetman et al.) discusses the possible use of antibodies as catalysts, and presents data relating to the use of polyclonal serum in hydrolyzing o-nitrophenyl-beta-D-galactoside. The antibodies useful in that patent are said to be inducible by a reactant, a reaction intermediate or to an analog of the reactant, product or reaction intermediate. The term "analog" is there defined to encompass isomers, homologs or other compounds sufficiently resembling the reactant in terms of chemical structure that an antibody raised to an analog can participate in an immunological reaction with the reactant but will not necessarily catalyze a reaction of the analog.

The data provided in that specification only indicate that some cleavage of the substrate (reactant) galactoside occurred over an eighteen hour time period using a relatively concentrated antibody preparation (1:10 and 1:20 dilutions). Although catalysis was alleged, catalytic activity was not shown since no turn over of the allegedly catalytic antibody was shown, nor was there an indication of the percentage of substrate galactoside cleaved. The patent did indicate that beta-D-galactosidase cleaved about ten times as much substrate as did the polyclonal antibodies, presuming linearity of absorbance at the unnamed concentration of substrate studied.

From the data presented in that patent, it is possible that a nucleophilic replacement of the o-nitrophenyl group occurred by a terminal amino group of a lysine residue of the antibody preparation used. Thus, the observed absorbance could have been due to formation of epsilon-amino lysinyl o-nitrophenyl aniline or to the formation of an epsilon-amino-lysinyl galactoside and o-nitrophenol, either of which occurrences would not be catalytic since the antibody was consumed, rather than turning over.

U.S. Pat. No. 4,792,446 (Kim et al.) discusses the possible use of antibody catalysts in the synthesis of chiral molecules. However, such syntheses were neither described nor disclosed in that patent.

In more recent work, bimolecular amide formation catalyzed by antibody molecules has been disclosed [Benkovic et al., *Proc. Natl. Acad. Sci. USA*, 85:5355 (1988)], as has an antibody-catalyzed Claisen rearrangement [Jackson et al., *J. Am. Chem. Soc.*, 110:4841 (1988)]. None of that work, nor the previously discussed work, has contemplated the use of antibodies to catalyze any reaction in a stereospecific manner.

Stereospecificity was shown in an antibody-catalyzed lactone-forming reaction [Napper et al., *Science*, 237:1041 (1987)] and in an antibody-catalyzed Claisen reaction [Hilvert et al., *Proc. Natl. Acad. Sci. USA*, 85:4955 (1988)]. The use of paratope-containing molecule to catalyze a hydrolysis reaction of a meso compound to yield a product that is one of a pair of enantiomers as is described hereinafter was not, however, contemplated in any of the above publications.

BRIEF SUMMARY OF THE INVENTION

The present invention contemplates a receptor molecule that contains an antibody combining site or paratope-containing polyamide that catalytically hydrolyzes a preselected, scissile carboxylic acid ester bond of an achiral substrate meso diester reactant ligand. That antibody combining site binds to (immunoreacts with):
(a) A substrate meso diester reactant ligand containing that preselected scissile carboxylic acid ester bond and a meso compound nucleus containing at least 4 carbon atoms, and (b) an analog-ligand that has the same stereochemical configuration as the reactant ligand and that contains a tetrahedrally bonded phosphorus atom at a position analogous to that of the carbonyl carbon atom of the preselected scissile carboxylic acid ester bond of the substrate meso reactant ligand. The hydrolytic transition state of the substrate meso diester reactant ligand so bound contains a tetrahedral carbon atom bonded to (i) a carbon atom, the alpha carbon of the acid portion of the ester, (ii) two oxygen atoms, and (iii) the oxygen atom of an ester.

Molecules containing an antibody combining site that bind to the hydrolytic transition state of a substrate meso reactant ligand are raised or induced by immunizing with an analog-ligand molecule (preferably bound to a protein carrier to form a conjugate) having a stereochemical configuration that is the same as the substrate ligand and contains an analog of a hydrolytic transition state of the substrate ligand. The immunizing analog-ligand hydrolytic transition state molecule contains a tetrahedrally bonded phosphorus atom, bonded directly to (i) a carbon atom of a carboxylic acid portion of the analogous meso diester reactant ligand (the alpha-carbon of the acid portion), (ii) two oxygen atoms, and (iii) a third oxygen atom that is bonded to a carbon atom of the alcohol portion of the analogous ligand ester (the alpha-carbon of the alcohol portion).

The alpha-carbon atom of the acid portion, (i) above, bonded directly to the central tetrahedral phosphorus atom of the analog-ligand molecule, is included in a radical that contains at least one carbon atom, and more preferably contains 4 to about 8 carbon atoms and associate hydrogens. Of the two oxygen atoms [(ii) above] bonded directly to the central atom, one oxygen atom is bonded twice (doubly bonded) in an oxo group to the central atom. The second of those oxygen atoms bonded to the central atom is singly bonded to the central atom and is also bonded to a hydrogen, a $C_1$–$C_4$ alkyl radical or is an oxy group ($O^-$) neutralized by an alkali metal cation. The fourth atom, (iii) above, bonded to the central atom of the analog-ligand molecule corresponds to the alcohol oxygen atom of an ester of the analogous ester portion of the ligand. That fourth atom (third oxygen) is also bonded to a radical that contains at least one carbon atom, and more preferably contains 1 to about 10 carbon atoms along with attendant hydrogen atoms. At least one of the alcohol and carboxylic acid portions of the meso diester substrate ligand and corresponding analog-ligand contains at least 4 carbon atoms.

It is emphasized that both the substrate meso compound and analog-ligand contain at least two carbon atoms that can exist in two stereoisomeric forms, and thereby provides a potential stereoisomeric center. That potential stereoisomeric center is located in each of the substrate meso diester compound and analog-ligand molecules at the same relative position in each molecule. The potential stereoisomeric center is also located near enough to the bond to be hydrolyzed so that the potential stereoisomeric center is bound by the catalytic antibody combining site-containing molecule.

The tetrahedrally bonded central atom is phosphorus of a phosphonate group so that the analog-ligand is an organophosphorus compound with an arrangement of substituents about the phosphorus atom that corresponds to the tetrahedral carbon transition state for ester hydrolysis of the meso diester substrate ligand. A phosphonate monoacid in its ionized form also simulates the developing charge in nucleophilic attack at a carbonyl center.

In the studies described herein, phosphonate esters function as transition state analogs to induce antibodies that are monoclonal and that are asymmetry-inducing carboxylic esterases. In effect, these antibodies express their inherent binding energy functionally, as true enzymes, to catalytically hydrolyze esters, and classically, as antibodies, to bind antigens.

A meso diester substrate ligand can be expressed by structural Formula I as:

wherein

W is (i) $CO_2$— or (ii) $O_2C$—;

X is (i) —$CO_2$ or (ii) —$O_2C$, with the proviso that where W is $CO_2$—, X is —$O_2C$, and where W is $O_2C$—, X is —$CO_2$;

$R^2$ is an alkyl, aralkyl or aromatic radical containing at least 1 carbon atom, and more preferably 1 to about 10 carbon atoms and attendant hydrogen atoms; and $R^1$ is a meso compound nucleus that contains 4 to about 8 carbon atoms and attendant hydrogen atoms.

A corresponding analog ligand can therefore be expressed by structural Formula II as:

wherein a, b, c and d are the numerals one and zero such that when any of a–d is one, the adjacent group W–Z is present, and when any of a–d is zero, the adjacent group W–Z is absent, with the provisos that:

(a) when either of a and c is one, the other is zero;

(b) when either of b and d is one, the other is zero; and (c) when either of a or b is one, the other is zero;

W is (i) $CO_2$— or (ii) $O_2C$—;

X is (i) —$CO_2$ or (ii) —$O_2C$, with the proviso that where W is $CO_2$—, X is —$O_2C$, and where W is $O_2C$—, X is —$CO_2$;

Y is (i) $P(O)(OR^3)O$— or (ii) $O(R^3O)(O)P$—;

Z is (i) —$O(R^3O)(O)P$ or (ii) —$P(O)(OR^3O$, with the proviso that where (a) w is $CO_2$—, Z is —$O(R^3O)(O)P$;

(b) W is $O_2C$—, Z is —$P(O)(OR^3)O$;

(c) X is —$CO_2$, Y is $O(OR^3)(O)P$—; and (d) X is —$O_2C$, Y is $P(O)(OR^3)O$—;

$R^3$ is H (hydrogen), $C_1$–$C_4$ alkyl or an alkali metal salt; and $R^1$ and $R^2$ are as defined previously, except that one of the $R^2$ groups of an analog-ligand preferably further includes a group or radical through which a haptenic analog-ligand can be linked to an antigenic carrier for purposes of immunization, as noted hereinafter.

A method of preparing monoclonal receptor molecules that bind to the hydrolytic transition state of a particular ester is also contemplated. Here, a before-described haptenic analog-ligand molecule containing a hydrolytic transition state analog is provided linked to a carrier as an immunogenic conjugate. The conjugate thus provided is dissolved or dispersed in a physiologically tolerably diluent to form an inoculum. The inoculum is introduced as by injection into a suitable, non-human mammalian host in an amount sufficient to induce antibodies to the haptenic analog-ligand.

The antibodies so induced are harvested. The harvested antibodies are assayed for their ability to bind to (immunoreact with) the immunizing, haptenic ligand analog. Immunoglobulin-producing cells such as those from the spleen of an animal whose antibodies bind to the immunizing, haptenic analog-ligand are collected and are fused with myeloma cells to form hybridoma cells. The hybridoma cells are grown in a culture medium and the supernatant medium from the growing hybridoma cells is assayed for the presence of antibodies that bind to the immunizing, haptenic analog-ligand.

Hybridoma cells whose supernatant contains such binding antibodies are then screened to determine which of those cells secreted antibodies that also hydrolyze the substrate meso reactant ligand in a manner that yields a product that is one of a pair of enantiomers. Hybridoma cells whose secreted antibodies bind to the immunogen, bind to a substrate meso reactant ligand and hydrolyze a substrate meso reactant ligand to yield a product that is one of a pair of enantiomers are then cloned to provide the desired monoclonal antibodies from culture medium supernatant or from the ascites of a host mammal into which the hybridoma is introduced.

The present invention provides several benefits and advantages. One benefit is the preparation of receptors whose binding site topological requirements are tailored to a particular substrate meso diester reactant ligand to be reacted and hydrolyze a preselected bond to yield a product that has the asymmetric configuration of one of a pair of enantiomers.

Another benefit of the present invention is the preparation of receptors that hydrolyze the ester substrate meso diester reactant ligand at a predetermined site to produce only one of a pair of enantiomers of the hydrolyzed derivative of the substrate meso diester reactant or substrate ligand and that exhibit catalytic properties.

An advantage of the invention is that because of the stereospecificity of the receptors that can be produced, a ligand containing a plurality of different hydrolyzable bonds can be hydrolyzed at a preselected, particular hydrolyzable bond.

Yet another advantage of the present invention is the provision of receptors that can selectively remove a blocking group from a meso diester compound during or after synthesis, thereby facilitating recovery or use, respectively, of a compound that is one of a pair of enantiomers.

Still further benefits and advantages of the present invention will be apparent to those skilled in the art from the discussion that follow

DETAILED DESCRIPTION OF THE INVENTION

I. Introduction

The present invention relates to molecules collectively referred to as receptors that are antibodies and idiotype-containing polyamide (antibody combining site or paratopic) portions induced by an analog of a substrate meso reactant ligand carboxylic acid ester that mimics the stereochemistry and conformation of the transition state in the reaction sequence for the hydrolysis of that substrate meso reactant ligand ester. The receptor molecules (antibodies and antibody combining sites) bind to one stereoisomer of the analog-ligand and to the substrate meso reactant ligand are thought to stabilize the hydrolytic transition state of a preselected portion of the substrate meso reactant ligand and thereby exhibit catalytic properties that produce only one of a pair of enantiomers of the hydrolyzed derivative of the meso reactant ligand.

Antibodies and enzymes are both proteins whose function depends on their ability to bind specific target molecules. Enzymatic reactions differ from immunological reactions in that in an enzymatic reaction the binding of the enzyme to its substrate typically leads to chemical catalysis, whereas a non-catalytic complex is the usual result of antibody-antigen binding.

Enzymes are believed to catalyze the hydrolysis of proteins by combining with the protein to stabilize the transition state of the hydrolysis reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W. P., *Adv. Enzymology*, 43, 219 (1975) and Pauling, L., *Amer. Scientist*, 36, 58 (1948)]. Support for this theory comes from the observation that substances that are thought to model the presumed transition states are often strongly bound to the enzymes as competitive inhibitors. Leinhard, G., *Science*, 180, 149 (1973) and Wolfenden, R., *Acc. Chem. Res.*, 5, 10 (1972). It is further thought that the enzyme accomplishes this lowering of the reaction free energy by binding the transition state geometry of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W. P., *XVII International Solvay Conference* (November 1983)].

The converse proposition is that an antibody that is prepared to optimally bind a suitable analog of a transition state would function as a catalyst. The demonstration of this result by Lerner and co-workers and Schultz and co-workers in the previously cited papers completes the correlation of enzyme function and antibody structure and provides a useful approach to devising artificial enzymes.

The basic idea behind immunological hydrolysis described herein contemplates the use of analog-ligands in the preparation of antibodies of predetermined specificity that preferentially bind to and thereby stabilize the transition state of ester bond hydrolysis upon binding to the specified substrate meso reactant ligand. An analog-ligand simulates the conformation of a high energy transition state in hydrolysis to induce the production of antibodies having the ability to bind related substrates and stabilize their hydrolyses.

Such preferential binding and stabilization results in a reduction in the activation energy for the hydrolysis reaction, thus meeting a criterion for catalysis. Antibodies that display this property can be obtained by immunization with synthetic analogs that are chemically modified to resemble the bonding characteristics of a substrate reactant ligand undergoing bond hydrolysis; i.e., by immunization with transition state analogs of the particular reaction.

In addition, a receptor molecule of the present invention also binds to and hydrolyzes a substrate meso reactant ligand to produce only one of a pair of enantiomers of the hydrolyzed derivative of the meso reactant ligand. Thus, where the substrate compound is meso, the product is only one of a pair of enantiomers of the hydrolyzed derivative of the meso compound.

Inasmuch as a receptor molecule of this invention induces asymmetry, both the analog-ligand and substrate meso diester reactant ligand contain at least two carbon atoms that can exist in two stereoisomeric forms; i.e., two stereoisomeric centers. The stereoisomeric centers are located in each of the analog-ligand and substrate meso diester reactant ligand molecules in the same positions relative to the other atoms in the analogous molecules. Thus, if one stereoisometric center is located in a chain four atoms away from the phosphorus atom in the acid portion of the analog-ligand, a stereoisomeric center is located in a chain four atoms away from the carbonyl carbon of the scissile ester bond of the substrate meso reactant ligand.

The two stereoisomeric centers can be on either the carboxylic acid or alcohol portions of the analog-ligand. If more than two such centers are present in the analog-ligand molecule, that plurality of stereoisomeric centers can be distributed in any way desired about the central phosphorus atom. Any stereoisomerism provided by the central tetrahedral phosphorus atom is not considered herein.

The substrate meso diester compound must, by definition, contain at least two stereoisomeric centers, each stereoisomeric center having the same atoms or groups attached to it. The number of stereoisomers in a molecule is determined by the equation: number of isomers $=2^n$, where n is the number of the stereoisomeric centers. According to the formula, the number of stereoisomers for a meso compound with two stereoisomeric centers (two chiral carbon atoms) should be $2^2$ or 4. However two of the four possible stereoisomers are in fact identical.

Thus, despite the presence of two stereoisomeric centers in a meso diester substrate ligand, the set of identical stereoisomers are not chiral. That set is in fact a single molecule and defines a meso compound, which is recognizable by its plane of symmetry.

In the case of the present invention where a substrate ligand is a meso diester, perturbation of this symmetry by hydrolysis of one of one portion creates two chiral centers, and the product molecule is no longer meso. As such, the two potential stereoisomeric centers of a meso compound can also be referred to as prochiral centers.

A receptor molecule of the present invention distinguishes and catalyzes the hydrolysis of a substrate meso reactant ligand to produce one of a pair of enantiomers that is a hydrolyzed derivative of the meso reactant ligand. This hydrolysis converts one selected prochiral center into a stereoisomeric center having an R or S configuration.

The above asymmetric induction by catalytic hydrolysis presumes that the locus of asymmetry, the prochiral center, is present in the substrate meso reactant ligand near enough to the bond to be hydrolyzed (the scissile ester bond) so that the prochiral center is bound by the catalytic antibody combining site-containing molecule. The receptor molecule may bind to one or both prochiral centers, but hydrolyses the preselected ester bond of only one prochiral center of the substrate meso reactant ligand.

The locus of the hydrolyzed bond is determined by the location of the phosphorus atom bonded directly or indirectly to a prochiral center of the analog-ligand (and the analogous carbonyl carbon of the scissile ester of the substrate meso reactant ligand) and the size of an antibody combining site. An antibody combining site is normally considered to be able to accommodate about five to about seven amino acid residues.

This analogous phosphorus-bonded prochiral center is within the volume occupied by one to about four amino acid residues (a chain length of about 12 atoms), and more preferably one to about two amino acid residues (a chain length of about six atoms) on either side of the phosphorus atom of the analog-ligand (carbonyl carbon of the scissile ester bond of the substrate meso compound). Thus, the prochiral center can be on the carboxylic acid portion or on the alcohol portion of the scissile ester bond of carboxylic acid diester substrate meso reactant ligand. In the exemplary meso diester used herein, the prochiral center is located in the alcohol portion of the molecule.

The above volume or chain length distance can readily be determined by use of space-filling models, or where there is doubt, by determining whether a catalytic receptor can hydrolyse a substrate meso diester reactant ligand to perturb the prochiral center to produce one of a pair of enantiomers.

In the exemplary catalytic reaction discussed hereinafter, the haptenic analog ligand was one of an enantiomeric, R, S, pair. The analog-ligand utilized in this exemplary study contained one enantiomer and induced production of receptor molecules that stereoselectively hydrolyzed the substrate meso diester reactant to induce production of one enantiomeric product.

The mechanism by which an antibody hydrolyzes an ester bond of a bound reactant ligand can be thought of in terms of an "induced fit" model. As the loosely bound substrate distorts or rearranges to conform to the binding geometry of the antibody, stress can be relieved by chemical reorganization of a single, predetermined amide or ester bond such that this reorganization leads to the hydrolysis of the bond.

The term "receptor" is used herein to mean a biologically active molecule that binds to a reactant ligand, inhibitor ligand, or analog-ligand. The receptor molecules of the present invention are antibodies, substantially intact antibodies or paratope-containing polyamide portions of an antibody.

Biological activity of a receptor molecule is evidenced by the binding of the receptor to its antigenic reactant ligand, inhibitor ligand or analog-ligand upon their admixture in an aqueous medium, at least at physiological pH values and ionic strengths. Preferably, the receptors also bind to an antigenic ligand within a pH value range of about 5 to 9, and at ionic strengths such as that of distilled water to that of about one molar sodium chloride.

Idiotype-containing polyamide portions (antibody combining sites or paratopes) of antibodies are those portions of antibody molecules that include the idiotype, and bind to the ligand or analog-ligand. Such portions include the Fab, Fab', Fv and F(ab')$_2$ fragments prepared from antibodies by well-known enzymatic cleavage techniques. See for example, U.S. Pat. No. 4,342,566 to Theofilopoulos and Dixon, generally, and specifically, Pollack et al., [Science, 234, 1570 (1987)] who reported accelerated hydrolytic rates for Fab fragments were the same as those of the native immunoglobulin. Inasmuch as the antibodies from which idiotype-containing polyamides are obtained are described as raised against or induced by immunogens, idiotype-containing polyamide (antibody combining site-containing) receptors are discussed as being "raised" or "induced" with the understanding that a cleavage step is typically required to obtain an idiotype-containing polyamide from an antibody. Intact antibodies are preferred, however, and are utilized as illustrative of the receptor molecules of this invention.

The receptors useful in the present invention are monoclonal antibodies. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monoclonal antibodies of the present invention are well known. Such receptors were first described by Kohler and Milstein, *Nature*, 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

A "ligand" is defined herein as a molecule that immunoreacts with or binds to a receptor molecule antibody combining site. Two types of ligand are contemplated herein. A first is termed an analog-ligand and is used as an immunogen (hapten) to induce preparation of receptor molecules and as an inhibitor of the receptor molecule-catalyzed reaction. The analog-ligand is substantially inert to undergoing the catalyzed reaction. The second is referred to as the reactant ligand or substrate ligand and is a meso diester molecule that undergoes that catalyzed hydrolysis reaction.

As described herein, chemical analogs of diester substrate ligands are synthesized that incorporate phosphonate moieties at specific, predetermined sites to mimic the conformation of the transition state in the hydrolysis of an ester bond. Such analogs are suitable candidates for this investigation because it is known that phosphonamidates have been used as transition state analogs in the inhibition of proteolytic enzymes [Bartlett, et al., *Biochemistry*, 22, 4618 (1983)].

Short polypeptide chains can induce the production of antibodies that recognize and bind to a homologous protein at a predetermined specific site. The present invention carries the earlier work with polypeptides a major step forward. Here, the antibodies (receptors) are induced by one stereoisomer of an immunizing haptenic first molecule (the analog-ligand), and recognize and bind not only to that first molecule, but also to a meso diester compound of a second, structurally similar (structurally congruent) molecule (the meso diester reactant ligand).

In binding that second molecule, the receptor causes hydrolysis (which as demonstrated herein is catalytic) of a preselected, ester bond that corresponds in topology to the topology of the immunizing, haptenic first molecule. The correspondence in topology; i.e., size, shape, stereochemistry and charge, provides a means for preselecting the site at which hydrolysis of the substrate ligand occurs as well as providing a means for perturbing the prochiral center of the meso reactant ligand to yield a chiral product that is one of a pair of enantiomers. Inhibitor ligands that resemble the structure of an analog-ligand or a meso diester reactant ligand are also bound by receptor molecules.

Consequently, by synthesis of a relatively small, immunizing haptenic analog-ligand, one can induce the production of receptor molecules that recognize, bind to and catalytically cleave an ester bond in another molecule that can contain a plurality of ester bonds. Thus, a receptor can be prepared that causes hydrolysis of a selected, predetermined ester bond of a model meso diester compound and yields a product that is one of a pair of enantiomers.

The implication of this result is that one can confer the activity of hitherto unknown esterases to immunoglobulins. Furthermore, the activity of the antibody combining site can be directed to any predetermined site at will by designating the ester bond to be cleaved with the phosphonate configuration in the haptenic analog-ligand used for immunization.

Thus, antibodies and idiotype-containing polyamide portions of antibodies are induced by a haptenic ester analog-ligand hydrolytic transition state molecule. The haptenic molecule contains a tetrahedrally bonded central phosphorus atom bonded directly to (a) a carbon atom of the carboxylic acid portion of the analogous ester (b) two oxygen atoms and (c) a third oxygen atom that is bonded to a carbon atom (the alpha-carbon) of the alcohol portion of an analogous ester of the ligand.

II. Transition State of Esterolysis and Hapten (Analog-Ligand) Design

Design of the analog-ligand flows backward from the structure of the product to be formed through the transition state for bond cleavage to be mimicked, and then to the analog-ligand. Reactions that involve amide or ester hydrolysis provide illustrative examples of the general concept and are utilized herein as exemplary for an ester hydrolysis reaction.

Transacylation processes are characterized by carbonyl addition-elimination mechanisms. The acyl group may, therefore, possess varying degrees of tetrahedral character in this transition state. W. P. Jencks, *Catalysis in Chemistry and Enzymology*, ch. 10, (McGraw-Hill, New York, 1969). The enzymes that catalyze transacylation reactions might be expected to bind well those analogs of the reactant ligand having a tetrahedral configuration about the acyl center. This is true for serine proteases, where a covalent bond between the ligand (substrate) and the enzyme is formed temporarily [Westerik et al., *J. Biol. Chem.*, 247, 8195 (1972); R. C. Thompson, Biochemistry, 12, 47 (1973) and Imperali et al., *Biochemistry*, 25, 3760 (1986)], as well as for enzymes that catalyze the direct hydration of amides or esters. The latter category is inhibited by compounds with a tetrahedral configuration including a phosphate, phosphonate or phosphonamidate group in lieu of the scissile amide unit [Weaver et al., *J. Mol. Biol.*, 114, 119 (1977) and Jacobsen et al., *J. Am. Chem. Soc.*, 103, 654 (1981)].

Naturally occurring and synthetic substances containing phosphorus have been studied as inhibitors of metallopeptidases. In these enzymes, the transition state would appear to contain the hydrated amide in the coordination sphere of the metal ion [W. N. Lipscomb, *Acc. Chem. Res.*, 15, 232 (1982)]. A complete picture of a transition state analog might then have the phosphono group of an inhibitor as a ligand to a metal ion or some other polarizing site [Weaver et al., *J. Mol. Biol.*, 114, 119 (1977) and Christianson et al., *J. Am. Chem. Soc.*, 108, 545 (1986)]. The role of the metal ions in metallopeptidases, however, is not clearly understood. It may have a multiple function in amide hydrolysis where proton transfer steps among the tetrahedral intermediates may be rate-limiting [L. M. Sayre, J. Am. Chem. Soc., 108, 1632 (1986)].

The hydrolysis of carboxylic acid esters is a simpler example of transacylation that should also be approximated by the phosphonate-containing analog of the transition state. The binding of the charged phosphonate group may describe a stabilizing interaction in the transition state that would lead to catalysis. Ester hydrolysis reactions exhibit spontaneous rates under ambient conditions that are suitable for antibodies. Therefore, any small rate acceleration can be readily detected.

The structures of the analog-ligands and reactant ligands for this investigation were selected according to certain criteria. These included the availability and stability of the organophosphorus precursors, the corresponding carboxylic acid substrate, the convenience of the chemical synthesis for its preparation, and the adaptability to diverse schemes for immunological presentation.

A substrate ligand of the present invention can be depicted by structural Formula I.

$$R^2-WR^1X-R^2 \qquad I$$

wherein

W is (i) $CO_2-$ or (ii) $O_2C-$;

X is (i) $O_2C-$ or (ii) $CO_2-$, with the proviso that where W is $CO_2$, X is $O_2C-$, and where W is $O_2C-$, X is $CO_2-$;

$R^1$ is a meso compound nucleus that contains at least 4 carbon atoms, and preferably 4 to about 8 carbon atoms and their associated hydrogen; and $R^2$ is an alkyl, aralkyl or aromatic radical containing at least 4 atoms; i.e., one carbon atom and its attendant hydrogens, and more preferably contains one to about 10 carbon atoms and attendant hydrogens.

In examining the above formula, it is noted that an X group can be bonded to an $R^1$ group through an oxygen atom or through the carbonyl carbon atom. As a consequence, an unesterified $R^1$ group can be a dicarboxylic acid or a dialcohol. A meso compound nucleus is therefore an unesterified meso compound that lacks the oxygen atoms or carboxyl groups of the meso diester substrate ligand.

An $R^2$ group contains at least one carbon atom such that when X is a $-CO_2$ group (the unesterified meso compound is a dicarboxylic acid and the ester is a methyl ester, $R^2$ is $CH_3$. Similarly, when X is a $-O_2C$ group (the unesterified meso compound is a dialcohol) and the acid portion is a reaction product of acetic acid, $R^2$ is also $CH_3$.

An $R^2$ group can be a straight, branched or cyclic alkyl group and can contain one to about 10 carbon atoms. Exemplary alkyl groups include methyl, ethyl, isopropyl, allyl, t-butyl, pentyl, cyclopentyl, cyclohexyl, cyclohexenyl, 2-methylpentyl, hexyl, heptyl, octyl, nonyl, decyl, and the like. An $R^2$ group can also be an aromatic radical such as phenyl, m-toluyl, naphthyl, xylyl, and the like. Aralkyl radicals such as benzyl, phenethyl, p-methylbenzyl, and the like are also contemplated $R^2$ groups.

The meso compound nucleus can contain 4 to about 8 carbon atoms, and can be saturated or contain ethylenic unsaturation. The meso compound nucleus is that portion of the molecule that contains the two prochiral centers and excluses the alcohol oxygen atom or carboxyl carbonyl carbon of the preselected scissile ester bond. Exemplary meso compound nucleii are illustrated in the table hereinafter through the depicted wedge-shaped bonds. The illustrative meso compound nucleus used herein is shown below.

Exemplary cyclic meso compound nucleii include 1,2-cyclopentylene, 1,3-cyclopentylene, 1,3-cyclopent-4-enylene, 1,2-cyclohexylene, 1,2-cyclohexa-3,5-dienylene, 1,3-cyclohexylene, 1,3-cycloheptylene, 1,5-cycloheptylene, 1,5-cyclohept-6-enylene, 1,3-cyclohept-4,6-dieylene, 1,2- or 1,4-cyclooctylene, 1,2-cycloocta-5-enylene, 1,2-cycloocta-4,6-dienylene, 1,4-cycloocta-6-enylene, and the like. Exemplary acyclic meso compound nucleii include 2,3-butylene, 2,4-pentylene, 2,5- or 3,4-hexylene, 2,5-hex-3-enylene, 2,7-, 3,6- or 4,5-octylene, 4,5-octa-2,6-dienyl, and the like.

Exemplary alcohol and acid portions that can be used to prepare an illustrative meso diester substrate ligands are illustrated in the table below. Dashed lines are utilized in some structures to indicate that ethylenic double bonds can also be present without having to redraw the structures. The bonds at the prochiral centers are also drawn as projecting upwardly from the page with the understanding that the same compound could be drawn with bonds projecting downwardly by rotation about each compound's plane of symmetry. In addition, not all hydrogen atoms are shown for enhanced clarity.

| Exemplary Meso Ester Substrate Ligands | |
|---|---|
| Alcohol Portion | Acid Portion |
| HO⏥OH (cyclopentylene) | $H_3CCO_2H$ |
| HO⏥OH (cyclohexylene) | $(CH_3)_2CHCOOH$ |
| HO⏥OH (cycloheptylene) | $CH_3(CH_2)_6CO_2H$ |
| CH₃<br>\|<br>C◄OH<br>\|<br>C◄OH<br>\|<br>CH₃<br>cis | $PhCO_2H$ |
| CH₃<br>\|<br>H····C◄OH<br>\|<br>CH₂<br>\|<br>H····C◄OH<br>\|<br>CH₃ | $m$-ClPhCO₂H |
| CH₃CH₂OH | HO₂H⏥CO₂H |

| Exemplary Meso Ester Substrate Ligands | |
|---|---|
| Alcohol Portion | Acid Portion |
| PhOH | HO₂C-⌬-CO₂H (cyclohexene diacid) |
| PhCH₂OH | HO₂C-⌬-CO₂H (cycloheptene diacid) |
| CH₃(CH₂)₃CH₂OH | CH₃<br>\|<br>H''''C◀CO₂H<br>\|<br>CH₂<br>\|<br>H''''C◀CO₂H<br>\|<br>CH₃ |
|  | CO₂H<br>\|<br>C◀CH₃<br><br>C◀CH₃<br>\|<br>CO₂H |

Ph = Phenyl

Examination of structural Formula I should make it apparent that hydrolysis of one ester bond formed by one $R^2$—$XR^1$ linkage changes the prochiral, meso diester compound substrate ligand into a single chiral product. Hydrolysis of the other ester linkage ($R^1X$—$R^2$) forms the other chiral, enantiomer. If both ester groups are hydrolyzed a meso compound product results.

An exemplary meso diester substrate ligand utilized herein is cis-3,5-diactoxycyclopent-1-ene (Compound 1), whose structure is illustrated below, where Ac is acetate.

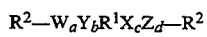

Using structural Formula I as a guide, an analog-ligand corresponds to structural Formula II, below.

$$R^2-W_aY_bR^1X_cZ_d-R^2 \quad \text{II}$$

wherein a, b, c and d are the numerals one and zero such that when any of a–d is one, the adjacent group W—Z is present, and when any of a—d is zero, the adjacent group W—Z is absent, with the provisos that:
(a) when either of a and c is one, the other is zero;
(b) when either of b and d is one, the other is zero; and
(c) when either of a or b is one, the other is zero;
W is (i) CO₂— or (ii) O₂C—;
X is (i) —CO₂ or (ii) —O₂C, with the proviso that where W is CO₂—, X is —O₂C, and where W is O₂C—, X is —CO₂;
Y is (i) P(O)(OR³)O— or (ii) O(R³O)(O)P—;
Z is (i) —O(R³O)(O)P or (ii) —P(O)(OR³O, with the proviso that where
  (a) W is CO₂—, Z is —O(R³O)(O)P;
  (b) W is O₂C—, Z is —P(O)(OR³)O;
  (c) X is —CO₂, Y is O(OR³)(O)P—; and
  (d) x is —O₂C, Y is P(O)(OR³)O—;
R³ is H (hydrogen), C₁-C₄ alkyl or an alkali metal salt; and
R¹ and R² are as defined previously, except that one of the R² groups of an analog-ligand preferably further includes a group or radical through which a haptenic analog-ligand can be linked to an antigenic carrier for purposes of immunization, as discussed hereinafter.

In accordance with structural Formulas I and II, the meso compound nucleus (R²) of a substrate ligand is bonded identically on either side of its plane of symmetry, as is an analog-ligand except for the replacement of the carbonyl carbon atom of the scissile ester bond with the tetrahedrally bonded phosphorus atom and its groups. It should also be noted from structural Formulas I and II that the absence of a depicted bond between W and R, and R and X and the depiction of that bond in the definition of W and X identifies the orientation of bonding of W and X and thereby identifies the meso diester substrate ligand as being the reaction product of a diacid or dialcohol. The corresponding absence and depiction of bonds for the Y and Z groups maintains that definition of the analog-ligand.

It should also be apparent from structural Formula II that only one phosphonate ester and only one corresponding carboxylic acid ester is present in an analog-ligand. The presence of either group requires the presence of the other for an analog-ligand.

By including an additional carboxylic acid, mercaptan or amine substituent in the acid or alcohol portion of the analog-ligand that does not include the meso nucleus, as in the acid portion of Compound C (below), the analog-ligand can be provided with a functional appendage for coupling to an antigenic (immunogenic) carrier protein. Such an added appendage is useful where the analog-ligand is a hapten, as is typically the case. The appendage and accompanying linking atoms can also be present in the reactant ligand, particularly where the reactant ligand is relatively small so that the antibody combining site can be relatively filled with the ligand.

An analog-ligand that provides the necessary features for asymmetric induction by catalytic hydrolysis is the 3,5-disubstituted cyclopent-1-ene ester analog ligand, Compound C, that is shown below.

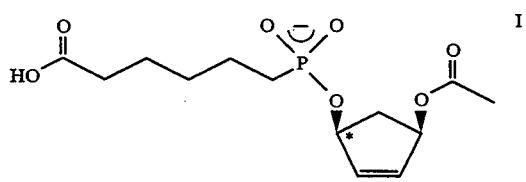

Compound C is shown in its haptenic form prior to coupling to an antigenic carrier for immunization. It should be noted that Compound C exists as one of a pair of enantiomers with its relevant stereoisomeric center identified by an asterisk (*), indicating that two stereoisomeric structures (R and S) are possible.

Thus, the present invention generally relates to monoclonal receptors, that catalytically hydrolyze a preselected ester bond of a substrate meso diester reactant ligand. The receptors contain an antibody combining site that binds: (a) to and catalyzes the hydrolysis of a meso diester reactant ligand that can form the tetrahedral hydrolytic transition state of a preselected ester bond of the reactant; i.e., contains a preselected scissile carboxylic acid ester bond, and (b) to and is induced by an analog-ligand that is one of a pair of enantiomers that has a tetrahedrally bonded phosphorus atom located at the position occupied by the carbonyl carbon atom of the preselected scissile ester bond of the meso diester reactant ligand substrate. The tetrahedrally bonded phosphorus atom is bonded directly to:

(i) a carbon atom (the alpha-carbon) of the acid portion of the analogous meso diester reactant ligand ester that is included in a radical chain that contains at least one carbon atom, and more preferably contains 4 to about 8 carbon atoms and attendant hydrogen atoms;

(ii) two oxygen atoms, one of which is bonded to the phosphorus atom by a double bond whereby the oxygen is an oxo radical, and the other of the two oxygen atoms is bonded singly to the phosphorus;

(iii) a third oxygen atom that is bonded to a carbon atom of the alcohol portion of the analogous ester; i.e., to the alpha-carbon of the alcohol portion of the ester, that is a portion of a radical that contains at least one carbon atom, and more preferably contains one to about 10 carbon atoms, along with attendant hydrogen atoms.

At least one of the alcohol and carboxylic acid portions of the analog-ligand (and meso diester substrate ligand) contains at least 4 carbon atoms; i.e., the portion containing the meso compound nucleus.

A meso diester substrate ligand can be prepared by straight forward procedures for esterification. Such methods include reaction of a meso dialcohol with two moles or more of an acid halide or anhydride, or by the reaction of a meso dicarboxylic acid halide such as an acid chloride with two moles or more of an alcohol. Of course, reaction conditions are selected for retention of the meso stereochemistry, as are well known.

Preparation of the analog-ligand is somewhat more complex, but is nevertheless also relatively straight forward. An exemplary synthesis of a meso diester analog ligand whose meso compound nucleus is derived from a dialcohol is provided hereinafter. Further syntheses of phosphonate derivatives that provide additional phosphorus-containing analogs of hydrolytic ester transition states can be found in U.S. Pat. Nos. 4,659,567 and 5,030,717, whose disclosures are incorporated by reference.

In a more general reaction, a tri $C_1$–$C_4$ alkyl phosphite is reacted with an appropriate alkyl halide such as a bromide to provide a dialkyl phosphonate ester. Reaction with oxalyl chloride forms a phosphonochloridate methyl ester. The latter compound is reacted with the alcohol portion in the presence of a non-nucleophilic strong base such as lithium diisopropylamide to form the analog-ligand as a monomethyl phosphonate ester. The monomethyl phosphonate ester is removed by treatment with a tempered amine such as tert-butylamine to provide a hydroxyl group salt, that can be neutralized with an acid such as hydrochloric acid that can also be exchanged to form a salt with an alkali metal hydroxide if desired.

The mono $C_1$–$C_4$ alkyl phosphonate ester group can also be removed by treatment with trimethylsilylbromide in chloroform. Exemplary $C_1$–$C_4$ alkyl groups of phosphonate ester include methyl, ethyl, isopropyl and butyl. Methyl is preferred.

As is noted elsewhere, the analog-ligand typically includes a group that is utilized to link the haptenic small molecule to an antigenic carrier molecule to form an immunogenic conjugate. That linking group is typically a part of the acid or alcohol portion that is other than that containing the meso compound nucleus.

Thus, as in the illustrative example utilized herein, the meso compound nucleus is present on the alcohol portion of the diester and the linking carboxyl group is present on the acid portion analogous to the acid portion that is catalytically hydrolyzed. Where the meso compound nucleus is present on the acid portion of the molecule, the linking group is preferably present on an alcohol portion, and that alcohol portion is preferably the alcohol portion that is hydrolyzed.

As a consequence of the requirements for immunization, the structure of an analog-ligand is analogous and not congruent with the structure of a substrate ligand. That lack of structural congruence includes the replacement of the carbonyl carbon atom of the scissile ester bond with the tetrahedral phosphorus atom as already discussed, and inclusion of the group used for linking to the antigenic carrier. The radical containing the linking group can also be somewhat different from the analogous radical in the substrate ligand with that difference typically being in the length of a chain or group that includes the linking group. Regardless of that lack of structural conguity, the substrate and immunizing ligands are structurally similar enough (analogs of each other) so that the induced antibody molecules bind to both.

An inhibitor ligand is also often used when studying the properties of a catalytic receptor. An inhibitor ligand is typically identical to an analog-ligand except that a linking group that would have an ionic charge in water at the pH values of the study is sometimes made to be free of ionic charge. For example, where the linking group of the analog-ligand is a carboxylic acid, the corresponding inhibitor ligand contains an ester or amide group of that carboxylic acid. Similarly, if the linking group is an amine, the inhibitor can have an amide prepared from that amine. The inhibitor ligand is free from ionic charge so that it more closely resembles the substrate ligand that is also free of ionic charge. In the present studies, Compound C, which bears an ionic charge at the pH values studied, was used as the inhibitor.

In another embodiment, this invention relates to a method of catalytically hydrolyzing a preselected ester bond in a meso diester reactant ligand molecule to yield a product that is one of a pair of enantiomers. The method comprises the steps of: (a) admixing a catalytically effective amount of one of the foregoing receptors with meso diester reactant ligand molecules that contain a prochiral center in an aqueous medium; and (b) maintaining the admixture for a period of time sufficient for the meso diester reaction ligand molecules to bind to the receptors and for the receptor molecules to hydrolyze the preselected bond of the meso diester reactant ligand to yield a product that is one of a pair of enantiomers. The product of that hydrolysis can be thereafter recovered, if desired.

A hydrolytic method of this invention utilizes an aqueous medium as a portion of the reaction admixture. That medium typically contains water and buffer salts. In addition, the medium can contain other salts such as sodium chloride, as well as water-soluble calcium and magnesium salts as are frequently found in protein-containing media. Organic solvents such as methanol, ethanol, acetonitrile, dimethyl sulfoxide, dioxane, hexamethylphosphoramide and N,N-dimethylforamide can also be present. Surface active agents that emulsify the reactant ligand and receptor molecule can also be present. The critical feature of ingredients present in the aqueous medium is that those ingredients not substantially interfere with or inhibit the catalytic reaction as by denaturation of the receptor molecule. Additionally, the aqueous medium is substantially free from salt, proteins generally, and enzymes, specifically, that inhibit the bond-breaking reaction catalyzed by the receptor molecule.

The aqueous medium typically has a pH value of about 5 to about 9, and preferably about pH 6.0 to about 8.0. pH Values greater and less than those recited values can also be utilized so long as the catalyzed reaction is again not substantially interfered with or inhibited.

The catalytic reactions are typically carried out at ambient room temperature; i.e., at about 20° to about 25° C. or at 37° C., and at an ambient atmospheric pressure; i.e., at about one atmosphere. However, temperatures down to about the freezing point of the aqueous medium and up to about the boiling point of the medium at atmospheric pressure can also be used. As is known, proteins such as the receptor molecule tend to denature at elevated temperatures such as those at which an aqueous medium boils, e.g., at about 100° C. and thus temperatures below about 40° C. are preferred. As is also well known, reactions that follow multimolecular kinetic expressions decrease in rate as the temperature decreases. Thus, a minimal temperature of about 15° C. is preferred.

The reactant ligand is present in a reaction mixture in an amount up to its solubility in the aqueous medium. A two phase system that includes insoluble reactant ligand can also be used, but normally is not so used. Normally used concentrations of the reactant ligand are about 0.1 micromolar ($\mu$M) to about 10 millimolar (mM), with that amount also being a function of the solubility of the reactant ligand in the solvent medium. Where the product is desired, per se, relatively higher concentrations are used as compared to lower concentrations where a reaction mechanism or reaction kinetics are to be studies.

An effective amount of the receptor molecule is also present. That effective amount is typically a catalytic amount; i.e., the receptor is used at a molar ratio to the reactant ligand of about 1:2 to about 1:10,000, with a molar ratio of about 1:10 to about 1:100 being preferred. The ratio of receptor molecule to reactant ligand typically depends upon the specific activity of the receptor molecule toward the reactant ligand and the purpose of the user in running the reaction.

Thus, where the product is desired, a relatively higher concentration of receptor and higher receptor to reactant ligand ratio are used. Where the reaction mechanism or kinetics of the reaction are being studied, a lower concentration and ratio are typically used. A stoichiometric amount of receptor or more can also be used, but since the receptor is a catalytic molecule, use of even a stoichiometric amount can be wasteful. Thus, at least a catalytic amount of the receptor is utilized.

The admixture formed from mixing receptor molecules and reactant ligand in an aqueous medium is maintained for a time period sufficient for the binding and reaction to occur. The duration of that maintenance period is a function of several parameters including the receptor and reactant ligand selected, their concentrations, pH value, and temperature, as well as what is being sought from the reaction.

Thus, where kinetic studies are being carried out, maintenance times of minutes to hours are frequently encountered. Where the reaction products are desired, maintenance times of hours to days are more usual.

III. Results

The enantiomeric Compound C covalently linked to KLH was used as an immunogenic conjugate to immunize mice. Hybridomas were prepared using spleen cells from an immunized animal.

Thirty-three hybridomas were prepared whose secreted monoclonal antibodies (receptors) were of the IgG isotype. Of those thirty-three monoclonals, one monoclonal receptor denominated 37E8, as was its secreting hybridoma denominated was capable of catalytically hydrolyzing the exemplary meso diester reactant (substrate) ligand Compound 1. The specific conditions used for the stereoselective hydrolyses are discussed hereinafter.

The structure of Compound C (shown before), as well as the intermediates in its synthesis is discussed hereinafter along with a discussion of the various syntheses involved herein.

The monoclonal antibody-mediated hydrolysis of the diacetate Compound 1 to form 3(R)-acetoxy-5(S)-hydroxycyclopent-1-ene (Compound 2) is shown below:

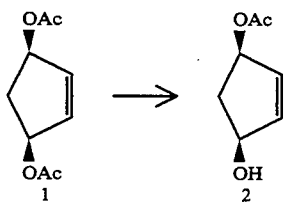

Compound 2, previously synthesized using Compound 1 and electric eel acetylcholinesterase [Deardoff et al., Tetrahedron Lett., 27, 1255 (1986); Johnson et al., J. Am. Chem. Soc., 111, 3456 (1989)], is useful as a starting material for a stereospecific total synthesis of prostaglandin $F_{2\alpha}$ and congeners thereof [Chow et al., J. Org. Chem 54, 6016 (1989)].

The production of Compound 2 by a monoclonal antibody composition of this invention was assayed at a concentration of 10 $\mu$M monoclonal antibody and 1 mM Compound 1 in pH 8.0 ATE buffer (0.52M ACES, 0.52M Tris, 0.01M ethanolamine) at 37° C. The initial rate of hydrolysis of Compound 1 by the monoclonal antibodies produced by hybridoma 37E8 followed Michaelis-Menten kinetics (Table 1 hereinafter).

In addition to monoclonal 37E8, possible sources of catalytic esterase activity in the reaction medium are the acetyl and butyl cholinesterases found in serum. Apart from the chromatographic data indicating virtually no contamination of the purified monoclonal antibodies with these esterases, further evidence of the lack of serum esterases in the monoclonal antibody preparation is provided by the large disparity between the inhibition constants ($K_i$) of authentic acetyl and butyl clorinesterase and the monoclonal antibody produced by hybridoma 37E8.

Inasmuch as the monoclonal antibodies were induced by Compound C, addition of free Compound C to a hydrolysis reaction catalyzed by the monoclonal antibodies of this invention should cause extensive inhibition. Conversely, addition of free Compound C to hydrolyses catalyzed by the authentic esterases should cause no inhibition. Table 1 shows that addition of free Compound C caused extensive inhibition of the hydrolytic reaction caused by monoclonal antibodies produced by hybridoma 37E8 ($K_i = 7.0 \times 10^{-6}$M), whereas the authentic acetyl and butyl cholinesterases showed no inhibition by free Compound C.

The conditions used for this study were as follows. Monoclonal antibodies produced by hybridoma 37E8 (10 μM) were added to a solution of 800 μM Compound 1 and 25 μM Compound C. Under these conditions, the substrate concentration was at saturation for the monoclonal antibody (4.5$K_m$) and at approximately $K_m$ for either cholinesterase.

TABLE 1

| Kinetic Parameters of Hydrolysis of Compound 1 | | | |
|---|---|---|---|
| Antibody Source/ Enzyme | $K_m(\times 10^{-6}$M) | $k_{cat}$(min$^{-1}$) | $k_i(\times 10^{-6}$M) |
| Hydridoma 37E8 | 177 | 0.007 | 7.0[c] |
| Acetyl Cholinesterase[a] | 620 | 250 | 630 |
| Butyl Cholinesterase[b] | 830 | 7.0 | 800 |

[a]EC 3.1.1.7. Type V-S, electric eel (Sigma Chemical Co., St. Louis), 1,000–2,000 units per mg protein, 0.059 units used.
[b]EC 3.1.1.8. From horse serum (Sigma Chemical Co., St. Louis), 500–1,000 units per mg protein, 0.0117 units used.
[c]Determined by S = $K_m$, $K_i$ = I, when velocity is equivalent to ½ $V_{max}$.

All assays consisted of determining the amount of Compound 2 by gas chromatography analysis (Hewlett Packard 5890A, carbowax 30 m, 0.53 mm bore, capillary column) with ethyl levulinate as an internal standard.

Additionally, the monoclonal antibody produced by hybridoma 37E8 (20 μM) showed less than 20 percent inactivation of the hydrolysis of 400 μM Compound 1 in the presence of 50 μM diisopropyl fluorophosphate (DFP), a powerful inhibitor of acetyl cholinesterase (Wilson et al., Proc. Natl. Acad. Sci. USA, 71, 3194 (1974)). The hydrolysis of 400 μM Compound 1 by authentic acetyl cholinesterase (2 μM) was completely inhibited by the same concentration of DFP.

The ability of a monoclonal antibody composition produced by hybridoma 37E8 to hydrolyze meso diester Compound 1 to yield a product that is one of a pair of enantiomers (Compound 2) was investigated by gas chromatographic analysis of a large scale reaction of that monoclonal antibody (40 μM) in pH 8.0 ATE buffer, containing 200 μM Compound 1. At selected times after the start of the reaction, 600 μl aliquots of the reaction mixture were removed, extracted twice with ethyl ether/ethyl acetate (50:50) and injected into a microcapillary gas chromatography column (Chrompack, CP-(optically pure)-Cyclodextran-B-236-M-19).

At eight hours after the start of the reaction, 60 μM Compound 2 was detected with an enantiomeric excess of 86 percent for Compound 2. After 14 hours of reaction, 100 μM Compound 2 was detected with an enantiomeric excess of 84 percent.

These results appear to be limited only by the catalytic activity of the monoclonal antibody produced by hybridoma 37E8. The inherent enantiotopic group selectivity of this monoclonal antibody is greater than 98 percent ee [calculated by correcting for the unwanted antipode to Compound 2, 3(S)-acetoxy-5(R)-hydroxycyclopent-1-ene, which came from the competing background hydrolysis ($8 \times 10^{-5}$ min$^{-1}$)].

It is believed that the above-described catalytic hydrolyses are the first such asymmetrically induced hydrolyses ever reported. It is further believed that this is the first report of the preparation of antibody combining site-containing receptor molecules that can catalyze a reaction of a meso diester compound to yield one member of a stereoisomeric pair; here, enantiomers. It is still further believed that this reaction is the first evidence of catalysis by an antibody combining site-containing molecule whose substrate ligand did not include an aromatic ring.

IV. Preparation of Analog-Ligands

It is noted that the syntheses discussed hereinbelow relate only to one meso carboxylic diester as reactant ligand and one phosphonate as analog ligand. However, those syntheses can be readily adapted for the preparation of different meso diester and phosphonate compounds by simple substitutions of reactants.

The specific synthesis discussed herein below is a significant extension of the method of preparing an antibody-combining site containing receptor molecule that can catalyze a chemical reaction. For example, there are no anchoring aryl substituents in the analog-ligand Compound C. Therefore, a decrease in the ability of Compound C to induce antibody formation was anticipated [Tijssen, P. in Practice and Theory of Enzyme Immunology (Burden et al., eds), Elsevier Press: New York, pp 39–41, (1987)].

The synthesis of analog-ligand Compound C in an enatiomerically pure form also presented a possible significant obstacle. The deprotonation of Compound B, below, might have resulted in racemization from acyl migration. Under the conditions described herein below, no racemization occurred as measured by $^{19}$F nuclear magnetic resonance of the crude Mosher ester Compound D.

The synthesis of Compound C, shown in Scheme I below, begins by reacting Compound A with trimethyl phosphite [P(OCH$_3$)$_3$] and p-cymene (isopropyltoluene) at 170° C. for 17 hours to yield a phosphonate derivative (62% yield; Reaction a). This phosphonate was then reacted with oxalyl chloride [(COCl)$_2$] and dichloromethane (CH$_2$Cl$_2$) at room temperature for six hours to provide a phosphonochloridate monomethyl ester (100 percent yield; Reaction b).

A cyclopentene ring was then added to the mixed anhydride of Reaction b by reaction with 3(R)-acetoxy-5(S)-hydroxycyclopent-1-ene and lithium diisopropylamide in tetrahydrofuran, increasing the temperature from −78° C. to zero degrees C over two hours. This yielded 55 percent of Compound B (Reaction c). Compound B was then reacted with trifluoroacetic acid and dichloromethane at room temperature for one hour to remove the phenyl ring-containing ester (90 percent yield; Reaction d) followed by tert-butylamine at 50° C. for two weeks to remove the phosphonate methyl ester, to yield 60 percent of Compound C (Reaction e).

The synthesis of the Mosher ester Compound D (Scheme II), made to verify that no acyl migration occurred in the synthesis of Compound C, began by reacting Compound B with sodium methoxide and methanol at zero degrees C for three hours to remove the acetyl group (Reaction f; 100 percent). A Mosher group was then added to the resulting compound by adding (R)-(+)-α-(trifluoromethyl)phenylacetyl chloride, pyridine, and dichloromethane, and reacting for three hours, increasing the temperature from −30° C. to room temperature over that time (Reaction g; 85 percent yield). The resulting compound was treated with tert-butylamine at 50° C. for two weeks to remove the phosphonate methyl ester, to yield 44 percent Compound D.

The carrier-hapten conjugate is dissolved or dispersed in an aqueous composition of a physiologically tolerable diluent such as normal saline, PBS, or sterile water to form an inoculum. An adjuvant such as complete or incomplete Freund's adjuvant or alum can also be included in the inoculum. The inoculum is intro-

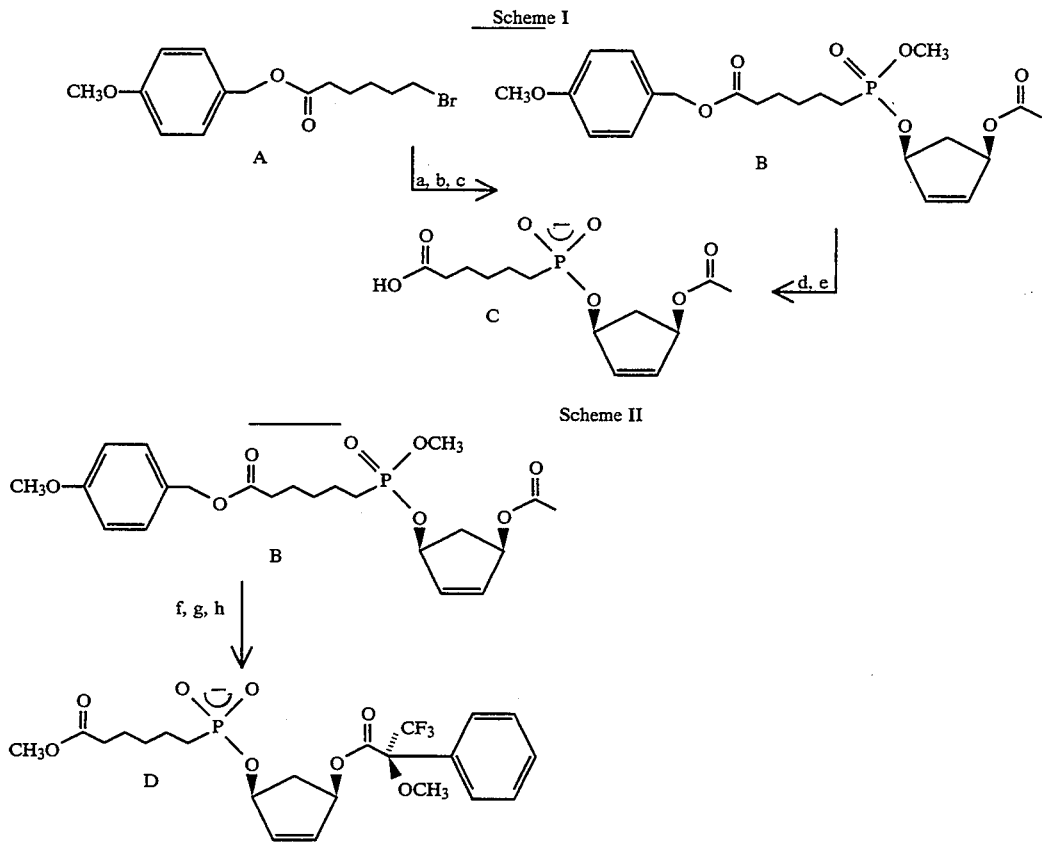

V. Preparation of Conjugates and Inocula

Conjugates of haptenic analog-ligand molecules with antigenic (immunogenic) protein carriers such as keyhole limpet hemocyanin (KLH) can be prepared, for example, by activation of the carrier with a coupling agent such as MBS (m-maleimidobenzoyl-N-hydroxy succinimide ester), and coupling to the thiol group of the analog-ligand. See, for example, Liu et at., Biochem., 80, 690 (1979). As is also well known in the art, it is often beneficial to bind a compound to its carrier by means of an intermediate, linking group.

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

The choice of carrier is more dependent upon the ultimate intended use of the antigen than upon the determinant portion of the antigen, and is based upon criteria not particularly involved in the present invention. For example, if the conjugate is to be used in laboratory animals, a carrier that does not generate an untoward reaction in the particular animal should be selected.

duced as by injection into the animal used to raise the antibodies in an amount sufficient to induce antibodies, as is well known.

In an exemplary procedure, 2.5 mg of a reaction product of haptenic analog-ligand containing an added alcohol or amine group for linking purposes and succinimidyl adipoyl chloride or succinimidyl glutaroyl chloride in 250 μl of dimethylformamide is slowly added to 2 mg of KLH in 750 μl of 0.01M sodium phosphate buffer at a pH value of 7.2. A temperature of 4° C. is utilized and the resulting admixture is stirred for about one hour to form the hapten-linked KLH conjugate. The conjugate reaction product so formed is thereafter purified by usual means.

In the present work Compound C (2 mg) was admixed with KLH (2 mg) in water (2 ml). The pH was adjusted to 4.5 with HCl and 10 equivalents of 1-ethyl-3-(3-dimethylaminopropyl)-carbodiimide were then added. The mixture was stirred for about 12 hours. The resultant crude product was injected into mice.

VI. Preparation of Monoclonal Receptors

The foregoing KLH conjugates (about 100 μg) were used to immunize mice (129G1X* strain), and monoclonal antibodies were obtained as described by Niman et al., Proc. Natl. Acad. Sci. USA, 77, 4524 (1980) and Niman et al., in Monoclonal Antibodies and T-Cell Products, Katz, D. H. ed., 23–51, CRC Press, Boca Raton, FL (1982). The lymphocytes employed to form the hybridomas of the present invention can be derived from any mammal, such as a primate, rodent (e.g., mouse or rat), rabbit, guinea pig, cow, dog, sheep, pig or the like. As appropriate, the host can be sensitized by injection of the immunogen, in this instance a haptenic analog-ligand, followed by a booster injection, and then isolation of the spleen.

It is preferred that the myeloma cell line be from the same species as the lymphocytes. Therefore, fused hybrids such as mouse-mouse hybrids [Shulman et al., *Nature*, 276, 269 (1978)] or rat-rat hybrids [Galfre et al., *Nature*, 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al., eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/0-Ag14 (ATCC CRL 1581), P3X63Ag8U.1 (ATCC CRL 1597), Y3-Ag1.2.3. (deposited at Collection Nationale de Cultures de Microorganisms, Paris, France, number 1-078) and P3X63Ag8 (ATCC TIB 9). The non-secreting murine myeloma line Sp2/0 or Sp2/0-Ag14 is preferred for use in the present invention.

The hybridoma cells that are ultimately produced can be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid were female 129G1X* mice bred in the mouse colony of the Scripps Clinic and Research Foundation, La Jolla, Calif.; however, when animals other than mice are used for preparation of the hybridomas, mice or that animal type can be used for the production of ascites fluid.

In particular, an exemplary monoclonal receptor was produced by the standard hybridoma technology of Kohler et al., *Nature*, 256, 495 (1975) and Engvall, E., *Methods Enzymol.*, 70, 419 (1980). Specifically, female 129GIX* mice were immunized by intraperitoneal injection with an inoculum of 100 micrograms of conjugate (e.g., Compound C bound to KLH) in 300 microliters of a 1:1 mixture of phosphate buffered saline (PBS), pH 7.4, and complete Freund's adjuvant. Two weeks later, the mice were again injected in a like manner with 50 micrograms of the foregoing conjugate in 300 microliters of a 1:1 mixture of PBS (pH 7.4) and 10 mg/ml alum. After an additional eight weeks, the mice were immunized intravenously with 50 micrograms of the conjugate in 200 microliters of PBS (pH 7.4). The spleens were removed from the mice four days later, and the spleen cells were fused to myeloma cells.

The spleens cells were pooled and a single cell suspension was made. Nucleated spleen cells ($1.4 \times 10^8$) were then fused with $3 \times 10^7$ Sp2/0-Ag14 non-secreting myeloma cells in the presence of a cell fusion promoter (polyethylene glycol 2000). A hybridoma that produces a particular monoclonal antibody was selected by seeding the spleen cells in 96-well plates and by growth in Dulbecco's modified Eagle medium (DMEM) containing 4500 mg/liter glucose (10 percent), 10 percent fetal calf serum (FCA), hypoxanthine, aminopterin and thymidine (i.e., HAT medium) which does not support growth of the unfused myeloma cells.

After two to three weeks, the supernatant above the cell clone in each well was sampled and tested by an ELISA assay (enzyme linked immunosorbent assay as described hereafter) for the presence of antibodies against Compound C. Positive wells were cloned twice by limiting dilution. Those clones that continued to produce Compound C-specific antibody after two clonings were expanded to produce larger volumes of supernatant fluid. The hybridoma and the monoclonal receptors produced therefrom and described herein are identified by the laboratory designation as discussed hereinafter.

A monoclonal receptor of the present invention can also be produced by introducing, as by injection, the hybridoma into the peritoneal cavity of a mammal such as a mouse. Preferably, as already noted, syngeneic or semi-syngeneic mammals are used, as in U.S. Pat. 4,361,549, the disclosure of which is incorporated herein by reference. The introduction of the hybridoma causes formation of antibody-producing hybridomas after a suitable period of growth, e.g. 1–2 weeks, and results in a high concentration of the receptor being produced that can be recovered from the bloodstream and peritoneal exudate (ascites) of the host mouse.

Although the host mice also have normal receptors in their blood and ascites, the concentration of normal receptors is typically only about five percent that of the monoclonal receptor concentration.

Monoclonal receptors are precipitated from the ascitic fluids, purified by anion exchange chromatography, and dialyzed against three different buffers.

The abundance of acetyl and butyl cholinesterase in red blood cells and serum [Stedman et al., *Biochem. J.* 26:2056 (1932); Alles et al., *Biol. Chem.*, 133: 375 (1940)] necessitated extra caution during purification of the antibody molecules. In the present study, IgG molecules were typically obtained from mouse ascites fluid via anion-exchange chromatography on a DEAE Sepharose column followed by affinity chromatography on a Protein G Sepharose column and then again by anion exchange chromatography on a Mono Q column. As a control, authentic acetyl and butyl cholinesterases were not retained in the affinity column when fractionated under the same conditions employed for antibody purification.

Antibodies obtained were judged to be greater than 98 percent homogeneous by sodium dodecyl sulfate polyacrylamide gel electrophoresis [Laemmli, V. *Nature*, 227:680 (1970)]. The resulting concentrated solutions containing isolated IgG fractions were typically prepared into stock solutions of receptor at 1–20 mg/ml using an appropriate buffer such as 50 mM Tris-HCl or sodium phosphate containing 0.01M sodium azide.

Of thirty-three anti-Compound C monoclonal receptors of the IgG isotype, one catalyzed the hydrolysis of substrate meso diester Compound 1. The hybridoma that produces the catalytic monoclonal receptor, given laboratory designation 37E8, was deposited at the American Type Culture Collection, 12301 Parklawn Drive, Rockville, Md. on Sep. 10, 1991 and was given ATCC accession number HB 10868.

The present deposit was made in compliance with the Budapest Treaty requirements that the duration of the deposit should be for 30 years from the date of deposit or for five years after the last request for the deposit at the depository or for the enforceable life of a U.S. patent that matures from this application, whichever is longer. The hybridoma will be replenished should it become non-viable at the depository.

A Fab fragment of a monoclonal receptor can be prepared from the purified receptor using predigested papain in a 0.1M sodium acetate buffer, at a pH value of 5.5, at 37° C., followed by reaction with iodoacetamide. The Fab fragment is typically further purified by anion exchange chromatography, dialysis, and DEAE anion exchange chromatography, and its homogeneity is judged by gel electrophoresis.

VII. Enzyme-linked Immunosorbent Assay (ELISA)

The binding of an analog-ligand by the induced monoclonal receptor molecule was assayed by ELISA with antibody at a fixed concentration in the range of its titer and varying inhibitor (free Compound C) concentration. Use of free Compound C as inhibitor helps to assure that an observed binding interaction is antigen-specific.

Assays were performed in flat-bottom polyvinyl microtiter plates (Dynatech, Alexandria, Va.). Illustratively, the wells were coated with a solution comprising Compound C bonded to BSA (as it was bonded to KLH) as the antigen ligand in phosphate buffered saline (PBS) using 50 microliters of solution per well. BSA was used as a carrier to bind the hapten to the cell wall, and an analog-ligand/BSA conjugate was used in place of the immunizing KLH-containing conjugate to screen out possible anti-KLH antibodies.

The bound ligands were coated at 1 microgram per milliliter. The plates were then incubated overnight at 37° C. in a dry oven. The dried plates were stored at 4° C. until use. Prior to the ELISA assay, dried plates were rehydrated by two washes of two minutes each with ten millimolar (mM) PBS, pH 7.4, containing 0.1 percent polyethylene sorbitan monolaureate (Tween 20) and 0.02 percent Thimerosal (sodium ethylmercurithiosalicylate), (Sigma, St. Louis, Mo.).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for one hour at 4° C. on a gyroshaker to contact the monoclonal antibody-containing supernatant with the bound Compound C. Following two washes of two minutes each, 50 microliters of peroxidase-labeled goat anti-mouse IgG+IgM (Tago, Burlingame, Calif.), diluted 1:1000, were added to each well, and the reaction mixture was incubated at 4° C. for one hour to bind the labeled antibody to bound monoclonal antibody.

The substrate used to assay bound peroxidase activity was prepared just prior to use and consisted of 400 microgram/ml o-phenylenediamine (Sigma, St. Louis, Mo.) in 80 mM citrate-phosphate buffer, pH 6.0, containing 0.12 percent $H_2O_2$. After two final washes, 50 microliters of substrate solution were added to each well, and color was allowed to develop for 15 minutes in the dark. Color development was stopped by adding 25 microliters of four molar $H_2SO_4$ to each well and the optical density at 492 nanometers (nm) was measured with a Multiskan ELISA plate reader.

For another preparation of the receptor molecules, the gene that encodes an antibody combining site-forming fragment can be obtained from any cell that produces an antibody molecule that immunoreacts as discussed herein. A preferred cell is a hybridoma cell.

For examples of general recombinant DNA cloning methods, see *Molecular Cloning*, Maniatis et al., Cold Spring Harbor Lab., New York, 1982; *DNA Cloning*, Glover, ed., IRL Press, McLean Va. (1985). For the genomic cloning and expression of immunoglobulin genes in lymphoid cells, see Neuberger et al., *Nature*, 312:604–8 (1984); Ochi et al., *Proc. Natl. Acad. Sci. USA*, 80:6351-55 (1987); and Oi et al., *Proc. Natl. Acad. Sci. USA*, 80:825–29 (1983). For cloning of immunoglobulin genes from hybridoma cells and expression in Xenopus oocytes, see Roberts et al., *Protein Engineering*, 1:59–65 (1986), and see Wood et al. for expression in yeast. *Nature*, 314:446-9 (1985).

The foregoing is intended as illustrative of the present invention but not limiting. Numerous variations and modifications can be effected without departing from the true spirit and scope of the invention.

What is claimed:

1. Monoclonal antibody molecules secreted by hybridoma 37E8 having ATCC accession number HB 10868, or paratope-containing portions thereof that catalytically hydrolyze a preselected carboxylic ester bond of a substrate meso diester reactant ligand containing two prochiral centers to yield a product that is one of a pair of enantiomers.

2. Hybridoma 37E8 having ATCC accession number HB 10868 that secretes a monoclonal antibody molecule containing a paratope that catalytically hydrolyzes a preselected carboxylic acid ester bond of a substrate meso diester reactant ligand containing two prochiral centers to yield a product that is one of a pair of enantiomers.

* * * * *